United States Patent [19]

Cragoe, Jr. et al.

[11] 4,145,551
[45] Mar. 20, 1979

[54] PYRAZINE-2-CARBONYLOXYGUANIDINES

[75] Inventors: Edward J. Cragoe, Jr., Lansdale; Otto W. Woltersdorf, Jr., Chalfont; Mark G. Bock, Hatfield, all of Pa.

[73] Assignee: Merck & Co., Inc., Rahway, N.J.

[21] Appl. No.: 868,104

[22] Filed: Jan. 9, 1978

[51] Int. Cl.$^2$ .................. A61K 31/495; C07D 241/28
[52] U.S. Cl. ..................................... 544/407; 424/250
[58] Field of Search ................................. 260/250 BN

[56] References Cited
U.S. PATENT DOCUMENTS

| 3,272,828 | 9/1966 | Esch et al. | 260/295 |
| 3,577,418 | 5/1971 | Cragoe et al. | 260/250 |

Primary Examiner—Alton D. Rollins
Assistant Examiner—Lisa Jones
Attorney, Agent, or Firm—Michael C. Sudol, Jr.; Harry E. Westlake, Jr.

[57] ABSTRACT

The case involves novel pyrazine-2-carbonyloxyguanidines and processes for preparing same. The pyrazine-2-carbonyloxyguanidines are eukalemic or antikaliuretic agents possessing diuretic and natriuretic properties.

5 Claims, No Drawings

PYRAZINE-2-CARBONYLOXYGUANIDINES

BACKGROUND OF THE INVENTION

The background to this invention, U.S. Pat. Nos. 3,313,813 and 3,577,418 patented Apr. 11, 1967 and May 4, 1971, respectively, which are isomers of compounds of the instant case, show novel (3-amino-5,6-disubstitutedpyrazinoyl)guanidine compounds and compounds which are isomers of the compounds in the instant case. The compounds of the U.S. Pat. No. 3,313,813 are useful because they possess diuretic and natriuretic properties. They differ from most of the known, effective diuretic agents, however, in that the compounds of the U.S. Pat. No. 3,313,813 selectively enhance the excretion of sodium ions while simultaneously causing a decrease in excretion of potassium ions. The potassium loss, which is caused by known diuretics, often results in a severe muscular weakness. Since the compounds of the U.S. Pat. No. 3,313,813 prevent the potassium depletion, they have this decided advantage as diuretics. As diuretic agents, they can be used for the treatment of edema, hypertension and other diseases or conditions known to be responsive to this therapy and are especially useful when used in combination with or concomitantly with potassium losing iuretic agents.

Applicants' instant compounds shown in Formula I subsequently differ from the compounds shown in U.S. Pat. No. 3,313,813 in structure. Further, U.S. Pat. No. 3,577,418 describes in Examples 87 and 116 compounds which are isomers of compounds of the instant case. The compounds of the instant case, however, are made by a different process than that shown in U.S. Pat. No. 3,577,418. Applicants have found that the pyrazine-2-carbonyloxyguanidines of the instant case change the pharmaceutical action and utility of these compounds.

In actuality, applicants' compounds in the instant case as further described, accomplish the objective previously achieved by using a combination of the pyrazinoylguanidine compounds of the U.S. Pat. No. 3,313,813 patent with diuretic agents which cause elimination of sodium with concomitant excessive potassium elimination. Thus, the effect of the insertion of an oxygen atom between the pyrazinoyl and the guanidino moieties of the pyrazinoylguanidine compounds of the U.S. Pat. No. 3,313,813 results in producing eukalemic and antikaliuretic saluretic agents. Since the compounds of the instant invention are thus eukalemic saluretic agents they constitute single entities which are useful for the treatment of edema and hypertension and other diseases or conditions known to be responsive to this therapy.

SUMMARY OF THE INVENTION

The instant case covers novel pyrazine-2-carbonyloxyguanidines and processes for making the same. The novel compounds of this invention are depicted in Formula I below.

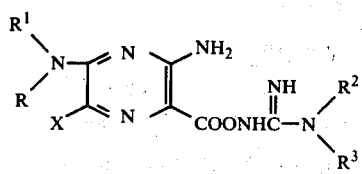

wherein
R is hydrogen, lower alkyl having from 1 to 5 carbon atoms such as methyl, ethyl, isopropyl, n-butyl or n-pentyl; lower alkenyl having from 2 to 5 carbon atoms such as allyl; lower alkynyl having from 2 to 5 carbon atoms such as propargyl;

$R^1$ is hydrogen, lower alkyl having from 1 to 5 carbon atoms such as methyl, ethyl, isopropyl, n-butyl or n-pentyl; lower alkenyl having from 2 to 5 carbon atoms such as allyl; lower alkynyl having from 2 to 5 carbon atoms such as propargyl;

$R^2$ is hydrogen, lower alkyl having 1 to 5 carbon atoms such as methyl, ethyl, isopropyl, n-butyl or n-pentyl; aryl, such as phenyl; aralkyl such as benzyl or phenethyl;

$R^3$ is hydrogen or lower alkyl having from 1 to 5 carbon atoms such as methyl, ethyl, isopropyl, n-butyl or n-pentyl;

$R^2$ and $R^3$ can be combined to form with the nitrogen atom to which they are attached a 4 to 6 carbon atom ring; and X is halo, such as fluoro, chloro, bromo or iodo.

Preferred compounds of this invention are those compounds of Formula I wherein
R is hydrogen or lower alkyl;
$R^1$ is hydrogen or lower alkyl;
$R^2$ is hydrogen;
$R^3$ is hydrogen; and
X is chloro.

The compounds of this invention as shown by Formula I and the preferred compounds discussed above are useful because they possess diuretic and natriuretic properties. In addition, they are useful eukalemic saluretics, in other words, the compounds of the instant case cause neither loss nor abnormal retention of potassium ions. Applicants' compounds combine in a single agent the advantages of a combination of the known pyrazinoylguanidine diuretics of U.S. Pat. No. 3,313,813 which decrease potassium with the known diuretics which cause a potassium loss. Thus, the compounds of this invention maintain the excretion of potassium at approximately normal levels while causing an increased renal elimination of sodium ions and water which is the desirable characteristic of the diuretic.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulations are merely combinations of the active ingredient mentioned with pharmaceutically inert carriers and the like.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The compounds disclosed in this invention in Formula I and the preferred compounds can be formed according to the process described below.

$$R^1\diagdown_{N}\diagup^{N}\diagdown_{N}\diagup^{NH_2}_{CO_2C=CH\ CONHC(CH_3)_3}\ +\ HONHC-N\diagup^{R^2}_{R^3}$$

(II)
$$\phantom{xxxx}(III)$$

$$R^1\diagdown_{N}\diagup^{N}\diagdown_{N}\diagup^{NH_2}_{COONHC-N\diagup^{R^2}_{R^3}}$$

(I)

wherein R, $R^1$, $R^2$, $R^3$ and X are as previously defined.

In this process, an ester compound (II) is reacted with a hydroxyguanidine (III) to form the desired product (I). The reaction is usually run in an inert solvent such as acetonitrile, isopropanol, ethanol or dimethylformamide generally at a temperature of from room temperature to the reflux temperature of the particular inert solvent used.

The reaction is usually run at from ½ to 2 hours. Extensive reflux generally causes rearrangement of the product. Generally a 1 to 1 mole ratio of the reactants (II) and (III) are also used.

The desired product (I) can be isolated from the reaction mixture by known methods such as by filtration or concentration of the reaction mixture.

The reaction conditions described above are critical, particularly the length of heating time; however, they can be varied within specified limits by those skilled in the art.

The starting materials (II) used in the process described above are shown in and disclosed in U.S. Pat. Nos. 3,313,813 or 3,577,418 mentioned previously or at least can be obviously prepared from compounds disclosed in the aforementioned patents.

Representative examples to illustrate this invention are the following:

EXAMPLE 1

3,5-Diamino-6-chloropyrazinecarbonyloxyguanidine

Sodium metal (3.1 g., 0.135 g.at.) is dissolved in 2-propanol (500 ml.) and hydroxyguanidine hemisulfate hydrate (20.0 g., 0.075 mole) is added. The reaction mixture is heated at reflux for 1 hour then treated with N-t-butyl-3-(3,5-diamino-6-chloropyrazinecarbonyloxy)-crotonamide (20.5 g., 0.06 mole) heated at reflux for an additional hour to give product which is filtered, washed with water and dried. 3,5-Diamino-6-chloropyrazinecarbonyloxyguanidine melts at 192°–3° C. after purification by precipitation from dilute aqueous methanesulfonic acid with aqueous ammonia.

Elemental analysis for $C_6H_8ClN_7O_2$: Calc.: C, 29.33; H, 3.28; N, 39.29; Found: C, 29.37; H, 3.38; N, 39.47.

EXAMPLE 2

By following substantially the procedure described in Example 1, but substituting for the N-t-butyl-3-(3,5-diamino-6-chloropyrazinecarbonyloxy)crotonamide therein described, an equimolar amount of the compounds shown in List 1 below, there is obtained an equivalent amount of the respective compounds shown in List 2 below.

List 1

N-t-butyl-3-(3-amino-5-methylamino-6-chloropyrazinecarbonyloxy)crotonamide;
N-t-butyl-3-(3-amino-5-ethylamino-6-chloropyrazinecarbonyloxy)crotonamide;
N-t-butyl-3-(3-amino-5-propylamino-6-chloropyrazinecarbonyloxy)crotonamide;
N-t-butyl-3-(3-amino-5-isopropylamino-6-chloropyrazinecarbonyloxy)crotonamide;
N-t-butyl-3-(3-amino-5-dimethylamino-6-chloropyrazinecarbonyloxy)crotonamide;
N-t-butyl-3-(3-amino-5-diethylamino-6-chloropyrazinecarbonyloxy)crotonamide.

List 2

3-amino-5-methylamino-6-chloropyrazinecarbonyloxyguanidine;
3-amino-5-ethylamino-6-chloropyrazinecarbonyloxyguanidine;
3-amino-5-propylamino-6-chloropyrazinecarbonyloxyguanidine;
3-amino-5-isopropylamino-6-chloropyrazinecarbonyloxyguanidine;
3-amino-5-dimethylamino-6-chloropyrazinecarbonyloxyguanidine;
3-amino-5-diethylamino-6-chloropyrazinecarbonyloxyguanidine.

EXAMPLE 3

By following substantially the procedure described in Example 1 but substituting for the N-t-butyl-3-(3,5-diamino-6-chloropyrazinecarbonyloxy)crotonamide therein described, an equimolar amount of the compounds shown in List 1 below, there is obtained an equivalent amount of the respective compounds shown in List 2 below.

List 1

N-t-butyl-3-(3,5-diamino-6-bromopyrazinecarbonyloxy)crotonamide;
N-t-butyl-3-(3,5-diamino-6-fluoropyrazinecarbonyloxy)crotonamide;
N-t-butyl-3-(3,5-diamino-6-iodopyrazinecarbonyloxy)crotonamide.

List 2

3,5-diamino-6-bromopyrazinecarbonyloxyguanidine;
3,5-diamino-6-fluoropyrazinecarbonyloxyguanidine;
3,5-diamino-6-iodopyrazinecarbonyloxyguanidine.

EXAMPLE 4

By following substantially the procedure described in Example 1 but substituting for the hydroxyguanidine hemisulfate hydrate therein described, an equimolar amount of an appropriate salt shown in List 1 below there is obtained an equivalent amount of the respective compounds shown in List 2 below.

List 1

1-hydroxy-2-methylguanidine;
1-hydroxy-2-ethylguanidine;
1-hydroxy-2-propylguanidine;
1-hydroxy-2-isopropylguanidine;
1-hydroxy-2-phenylguanidine;
1-hydroxy-2,2-dimethylguanidine;
1-hydroxy-2,2-diethylguanidine.

List 2

1-(3,5-diamino-6-chloropyrazinecarbonyloxy)-2-methylguanidine;
1-(3,5-diamino-6-chloropyrazinecarbonyloxy)-2-ethylguanidine;
1-(3,5-diamino-6-chloropyrazinecarbonyloxy)-2-propyl- -continued guanidine;
1-(3,5-diamino-6-chloropyrazinecarbonyloxy)-2-isopropyl-guanidine;
1-(3,5-diamino-6-chloropyrazinecarbonyloxy)-2-phenyl-guanidine;
1-(3,5-diamino-6-chloropyrazinecarbonyloxy)-2,2-dimethyl-guanidine;
1-(3,5-diamino-6-chloropyrazinecarbonyloxy)-2,2-diethyl-guanidine.

What is claimed is:
1. A compound of the formula

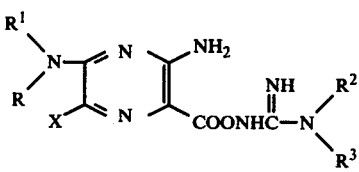

wherein
R is hydrogen, lower alkyl having 1–5 carbon atoms, lower alkenyl having 2–5 carbon atoms or lower alkynyl having 2–5 carbon atoms;
$R^1$ is hydrogen, lower alkyl having 1–5 carbon atoms, lower alkenyl having 2–5 carbon atoms, or lower alkynyl having 2–5 carbon atoms;
$R^2$ is hydrogen, lower alkyl having 1–5 carbon atoms, phenyl, benzyl, or phenethyl;
$R^3$ is hydrogen, or lower alkyl having 1–5 carbon atoms;
X is halogen.

2. A compound of the formula

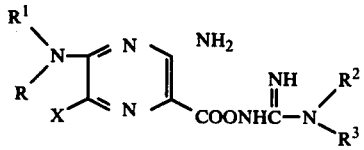

wherein
R is hydrogen or lower alkyl having 1–5 carbon atoms;
$R^1$ is hydrogen or lower alkyl having 1–5 carbon atoms;
$R^2$ is hydrogen;
$R^3$ is hydrogen; and
X is chloro.

3. A compound of claim 2 which is 3,5-diamino-6-chloropyrazinecarbonyloxyguanidine.

4. A compound of claim 2 which is 3-amino-5-dimethylamino-6-chloropyrazinecarbonyloxyguanidine.

5. A compound of claim 2 which is 3-amino-5-isopropylamino-6-chloropyrazinecarbonyloxyguanidine.

* * * * *